(12) United States Patent
Nakaji et al.

(10) Patent No.: US 9,446,098 B2
(45) Date of Patent: Sep. 20, 2016

(54) COMPOSITION FOR CONTROLLED RELEASE OF PHYSIOLOGICALLY ACTIVE SUBSTANCE

(71) Applicant: National University Corporation University of Toyama, Toyama-shi, Toyama (JP)

(72) Inventors: Tadashi Nakaji, Toyama (JP); Hiromi Kitano, Toyama (JP); Chirag Harsharan Singh Gujral, Belfast (GB)

(73) Assignee: National University Corporation University of Toyama (JP)

( * ) Notice: Subject to any disclaimer, the term of this patent is extended or adjusted under 35 U.S.C. 154(b) by 79 days.

(21) Appl. No.: 14/358,588

(22) PCT Filed: Nov. 9, 2012

(86) PCT No.: PCT/JP2012/079062
§ 371 (c)(1),
(2) Date: May 15, 2014

(87) PCT Pub. No.: WO2013/073454
PCT Pub. Date: May 23, 2013

(65) Prior Publication Data
US 2014/0377360 A1    Dec. 25, 2014

(30) Foreign Application Priority Data

Nov. 17, 2011  (JP) ................. 2011-251957

(51) Int. Cl.
*A61K 9/16* (2006.01)
*A61K 38/18* (2006.01)
(Continued)

(52) U.S. Cl.
CPC ............. *A61K 38/185* (2013.01); *A61K 9/167* (2013.01); *A61K 9/1641* (2013.01);
(Continued)

(58) Field of Classification Search
CPC ........ A61K 9/14; A61K 9/141; A61K 9/143; A61K 9/146; A61K 9/16; A61K 9/1605; A61K 9/1658
USPC ................ 424/489, 490, 491, 496, 497, 500
See application file for complete search history.

(56) References Cited

U.S. PATENT DOCUMENTS 5,753,234 A     5/1998 Lee et al.
2009/0186065 A1*  7/2009 Tillman ............... A61B 5/1405
                                                          424/423

FOREIGN PATENT DOCUMENTS

EP       2351556 A2      8/2011
EP       2351556 A2 *    8/2011    ............... A61K 9/12
(Continued)

OTHER PUBLICATIONS

Madduri et al (Collagen nerve conduits releasing the neurotrophic factors GDNF and NGF; Journal of Controlled Release, 143, 2010, 168-174).*

(Continued)

*Primary Examiner* — Micah-Paul Young
(74) *Attorney, Agent, or Firm* — Harness, Dickey & Pierce, P.L.C.

(57) ABSTRACT

A composition for controlled release of a physiologically active substance can release a physiologically active substance in vivo at the desired timing. The composition includes an inner layer that is formed of a biodegradable substance that supports a physiologically active substance, and an outer layer that is formed of a biodegradable substance that differs from that of the inner layer.

5 Claims, 12 Drawing Sheets

(51) Int. Cl.
*A61K 9/50* (2006.01)
*A61K 38/20* (2006.01)
*A61K 38/30* (2006.01)
*A61K 38/17* (2006.01)

(52) U.S. Cl.
CPC .......... *A61K 9/1647* (2013.01); *A61K 9/5031* (2013.01); *A61K 9/5036* (2013.01); *A61K 38/1709* (2013.01); *A61K 38/18* (2013.01); *A61K 38/1825* (2013.01); *A61K 38/1858* (2013.01); *A61K 38/1866* (2013.01); *A61K 38/2066* (2013.01); *A61K 38/30* (2013.01)

(56) References Cited

FOREIGN PATENT DOCUMENTS

| JP | 07-236688 A | 9/1995 |
| JP | 08-225454 A | 9/1996 |
| JP | 08-253426 A | 10/1996 |

OTHER PUBLICATIONS

Madduri, S., et al, "Effect of controlled co-delivery of synergistic neurotrophic factors on early nerve regeneration in rats", Biomaterials, 2010, vol. 31, No. 32, pp. 8402-8409.

Madduri, S., et al, "Collagen nerve conduits releasing the neurotrophic factors GDNF and NGF", J Control Release, 2010, vol. 143, No. 2, pp. 168-174.

Mundargi, R. C., et al, "Nano/micro technologies for delivering macromolecular therapeutics using poly (D,L-lactide-*co*-glycolide) and its derivatives", Journal of Controlled Release, 2008, vol. 125, pp. 193-209.

* cited by examiner (1)

(2)

(3)

(a) MPs (50 ug)

(b) MPs (100 ug)

(c) MPs (150 ug)

(a)

(b)

(a) COLD STORAGE (IN PBS)

(b) STORED IN FROZEN STATE (-30°C) (IN PBS)

(c) STORED IN LYOPHILIZED STATE (IN PBS)

COMPOSITION FOR CONTROLLED RELEASE OF PHYSIOLOGICALLY ACTIVE SUBSTANCE

CROSS-REFERENCE TO RELATED APPLICATIONS

This application is a U.S. National Stage Application of International Application No. PCT/JP2012/079062 filed on Nov. 9, 2012, and published in Japanese as WO 2013/073454 A2 on May 23, 2013. This application claims priority to Japanese Application No. 2011-251957 filed on Nov. 17, 2011. The disclosures of the above applications are incorporated herein by reference.

TECHNICAL FIELD

The present invention relates to a composition for controlled release of a physiologically active substance that can implement in situ control of delivery and release of a physiologically active substance in vivo.

BACKGROUND ART

A drug delivery system (DDS) has been extensively studied. In recent years, the results of controlled release of protein drugs have been reported (see Mundargi R. C., et al. Journal of Controlled Release, 2008, Vol. 125, pp. 193-209).

However, previous studies focus on suspended release of a drug over a long time, and a method that can implement in situ controlled release (e.g., release start timing) of a drug in vivo has not been reported.

For example, stem cell transplantation has been considered to be promising for the treatment of intractable diseases, and a number of studies have been conducted.

It has been considered that the progression of Parkinson's disease (i.e., central nervous system disease) can be stopped by drug therapy or the like, but a complete cure can be achieved only by neural stem/progenitor cell transplantation. Therefore, development of stem cell transplantation therapy has been strongly desired.

However, current stem cell transplantation therapy has a problem in that damaged tissue may not be able to control the transplanted stem cells, and may not be regenerated.

Although various methods have been studied, an effective method has not yet been developed.

It is well-known from molecular biological findings that stem cell differentiation is efficiently induced stepwise by a plurality of factors.

Specifically, it is indispensable to utilize the actions of a plurality of factors (e.g., factors A and B) stepwise at the desired timings in order to efficiently induce stem cell differentiation.

However, a protein DDS that can cause the functional factor to effect its action at the desired timing has not been developed.

This is considered to be because the major object of previous studies is to deliver proteins to the desired position, and effect suspended release of the proteins near the target cells (i.e., it has not been desired to control the action timing).

The inventors of the invention conducted studies in order to develop a protein delivery material that can implement in situ control of differentiation induction on the assumption that neural stem/progenitor cell transplantation therapy for the treatment of Parkinson's disease will make substantial progress through development of a material by which differentiation of transplanted stem cells can be efficiently induced, and tissue can be regenerated. The inventors thus developed the composition according to the invention.

SUMMARY OF THE INVENTION

Technical Problem

An object of the invention is to provide a composition for controlled release of a physiologically active substance that can release a physiologically active substance in vivo at the desired timing.

Solution to Problem

According to one aspect of the invention, a composition for controlled release of a physiologically active substance includes an inner layer that is formed of a biodegradable substance that supports a physiologically active substance, and an outer layer that is formed of a biodegradable substance that differs from that of the inner layer.

The term "controlled release" used herein means that the release start timing and the release rate of the physiologically active substance are controlled in vivo.

The term "physiologically active substance" used herein refers to a substance that shows activity in vivo, such as proteins, peptides, and neurotransmitters such as dopamine, serotonin, and L-dopa. Examples of a particularly effective physiologically active substance include nerve growth factor (NGF), glial cell-derived neurotrophic factor (GDNF), brain-derived neurotrophic factor (BDNF), neurotrophin-3, neurotrophin-4, insulin-like growth factor 1 (IGF-1), stem cell factor (SCF), and the like.

When the application is not limited to nerve cell differentiation, proteins such as basic fibroblast growth factor (bFGF), vascular endothelial cell growth factor (VEGF) (angiogenesis related factor), ciliary neurotrophic factor (CNTF), platelet-derived growth factor (PDGF) (that is effective for cells that construct an external environment that surrounds nerve cells), interleukin 10 (IL-10) (that suppresses inflammatory response) are also effective factors for cellular regulation.

The physiologically active substance is supported on the biodegradable substance that forms the inner layer utilizing a stable bond that does not inactivate the physiologically active substance.

The expression "stable bond" used herein refers to a bond due to specific intermolecular interaction between the physiologically active substance and the biodegradable substance that has an association constant of $10^8$ to $10^{10}$ M$^{-1}$.

When a protein is selected as the physiologically active substance, and collagen is selected as the biodegradable substance that forms the inner layer, the physiologically active substance can be stably supported on the biodegradable substance by utilizing a chimeric protein synthesis method that utilizes a genetic engineering technique.

For example, when a chimeric protein is fused with a collagen-binding peptide (CBP) at the C-terminal, the protein is supported on the collagen due to intermolecular interaction between the peptide and the collagen.

The protein is not inactivated when using this method.

For example, neural stem/progenitor cells are differentiated into immature nerve cells due to the effects of brain-derived neurotrophic factor (BDNF). In this case, glial cell-derived neurotrophic factor (GDNF) is considered to be unnecessary.

Specifically, a large amount of GDNF receptors are expressed by induction of differentiation, and GDNF is required after receptors have been expressed.

Therefore, it is effective to adjust the GDNF action timing to the timing of differentiation into mature nerve cells and dopamine nerve cells.

For example, when GDNF chimeric proteins are synthesized in which a collagen-binding peptide (CBP) is fused to the C-terminal of GDNF, and supported on collagen used for the inner layer, GDNF is not released as long as the inner layer (collagen) undergoes enzymatic or hydrolytic degradation. This makes it possible to control the release start timing of the physiologically active substance.

Therefore, it is preferable to use an outer layer that allows the physiologically active substance to pass through when the inner layer has undergone biodegradation.

It is preferable that the inner layer be formed of a natural biopolymer (e.g., collagen, gelatin, or hyaluronic acid), and the outer layer be formed of an amorphous biodegradable polymer.

Examples of the amorphous biodegradable polymer include polylactic acid (PLA), polyglycolic acid (PGA), polycaprolactone (PCL), a polyhydroxyalkanoic acid (PHA) (e.g., polyhydroxybutyric acid), poly(lactic-co-glycolic acid) (PLGA), and the like.

The outer layer is designed to finally disappear. The degradation rate of PLGA in vivo can be controlled by changing the mixing ratio of lactic acid and glycolic acid.

For example, when applying the composition for controlled release of a physiologically active substance according to one aspect of the invention to stem cell transplantation therapy, the composition for controlled release of a physiologically active substance is transplanted together with stem cells.

Therefore, it is preferable to prepare the composition for controlled release of a physiologically active substance in the form of microparticles having a size that can avoid phagocytosis by various cells such as immunocompetent cells in vivo.

It is necessary to prevent a situation in which the physiologically active substance is consumed by various cells in vivo before the physiologically active substance is released from the microparticles.

Therefore, it is preferable that the inner layer be an approximately spherical core that supports the physiologically active substance, and the outer layer be a layer that covers the core. It is more preferable that the average particle size be 5 to 60 µm.

The particle size is not particularly limited as long as phagocytosis does not occur.

The outer layer of each particle disappears after the physiologically active substance has been released.

Advantageous Effects of the Invention

Since the composition according to one aspect of the invention has a two-layer structure consisting of the inner layer and the outer layer that are formed of a biodegradable substance, and the physiologically active substance is supported on the inner layer, the outer layer physically protects the physiologically active substance supported on the inner layer, and the physiologically active substance is released upon biodegradation of the inner layer. Therefore, the composition can implement in situ control of release of the physiologically active substance in vivo at the desired timing.

It is possible to delay biodegradation of the inner layer by adjusting the thickness of the outer layer. Therefore, it is possible to strictly control the release timing.

The details thereof are described below.

It has been found that the half-life of collagen in vivo is about 10 days to about 2 weeks.

About 1 week is required for neural stem/progenitor cells to be differentiated into neural progenitor cells or early nerve cells, and they are differentiated into dopamine nerve cells upon reception of a GDNF signal.

Therefore, release of GDNF along with degradation of collagen occurs during differentiation, and differentiation can be efficiently induced.

When using a known protein DDS technique, GDNF is gradually released immediately after transplantation of neural stem/progenitor cells and microparticles.

However, GDNF is unnecessary for neural stem/progenitor cells immediately after transplantation, but is necessary for early nerve cells differentiated from the neural stem/progenitor cells.

GDNF is wasted due to unnecessary release, and may act on host-derived cells other than the transplanted cells (i.e., side effects may occur).

Moreover, it is likely that GDNF is depleted when GDNF is necessary.

The degraration rate of collagen can be adjusted by controlling the thickness of the biodegradable polymer (e.g., PLGA) that forms the outer layer, and the microparticles disappear when several months has elapsed after release of GDNF due to biodegradation of collagen.

DESCRIPTION OF EMBODIMENTS

Experimental (preparation) examples in connection with the composition according to the embodiments of the invention are described below.

Experiment 1

Preparation of Protein-Containing Microparticles

Microparticles (composition) were prepared using a Water/Oil/Water double emulsion method.

A chloroform solution including 4% PLGA and 0.1% Pluronic-F68 (manufactured by SIGMA ALDRICH, polyethylene glycol-polypropylene glycol-polyethylene glycol block copolymer) was used as an oil phase, and an aqueous solution including 0.5% collagen and 0.1% Pluronic-F68 was used as a Water phase.

Collagen-binding peptide-fused glial cell-derived neurotrophic factor (GDNF-CBP) was added to the Water phase at a concentration of 20 μg/mL.

The solutions were mixed, and subjected to a micro ultrasonic treatment to prepare microparticles.

The resulting microparticle suspension was added dropwise to a 0.5% Pluronic-F127 (manufactured by SIGMA ALDRICH) aqueous solution, coated with a surfactant, and collected by centrifugation.

Note that the microparticles may be coated with a hydrophilic biodegradable polymer (e.g., polyvinyl alcohol).

The collected microparticles were fractionated by ultrafiltration or the like to obtain microparticles having a particle size of 5 to 40 μm.

Figure 1:
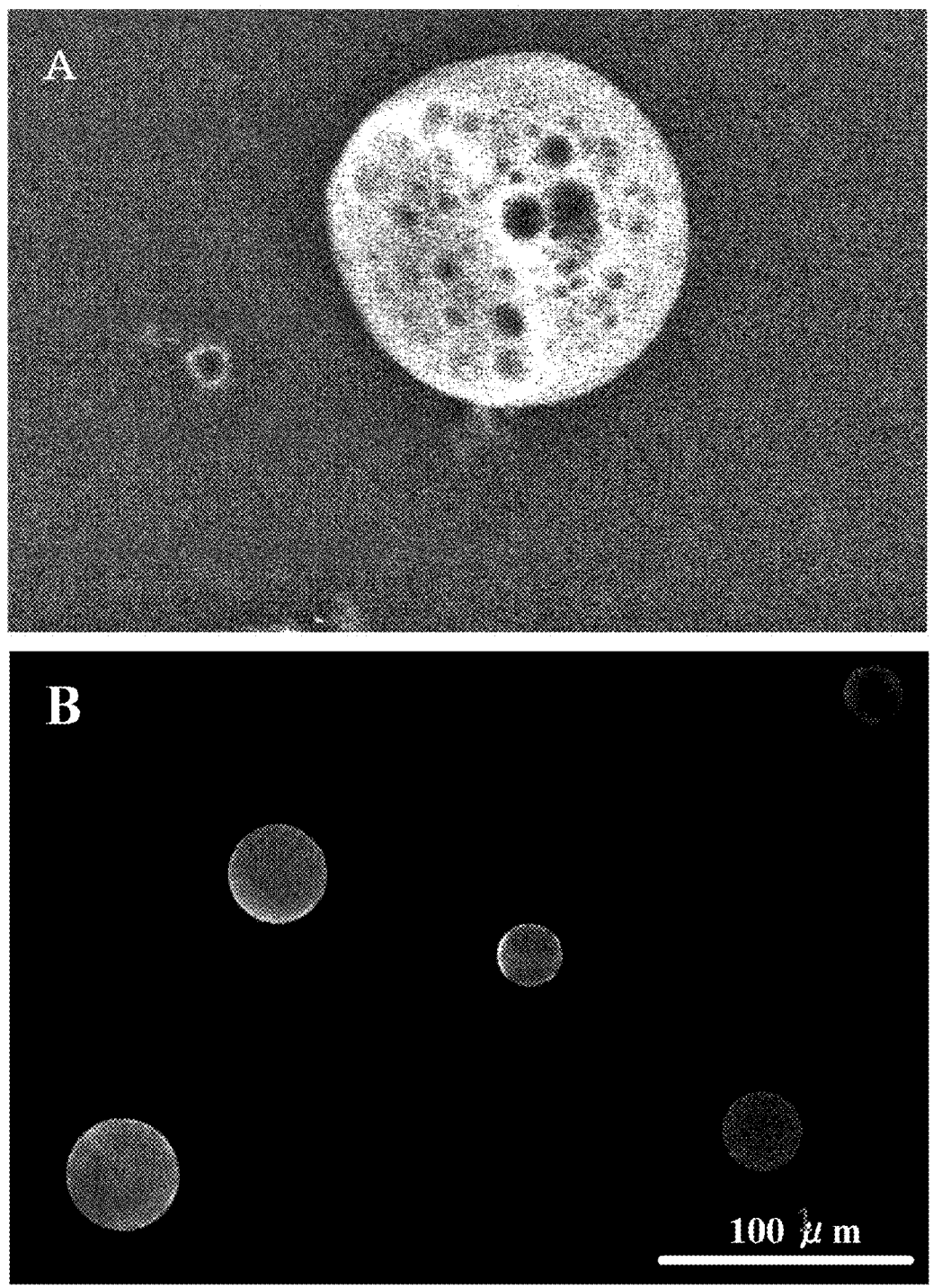
FIG. 1 shows a scanning electron phase-contrast micrograph of microparticles obtained after fractionation by ultrafiltration or the like (see (A)), and a fluorescence micrograph of microparticles containing red fluorescence-labeled GDNF-CBP (see (B)).

(A) in FIG. 1 is a scanning electron micrograph of the microparticles obtained after fractionation by ultrafiltration.

Figure 2:
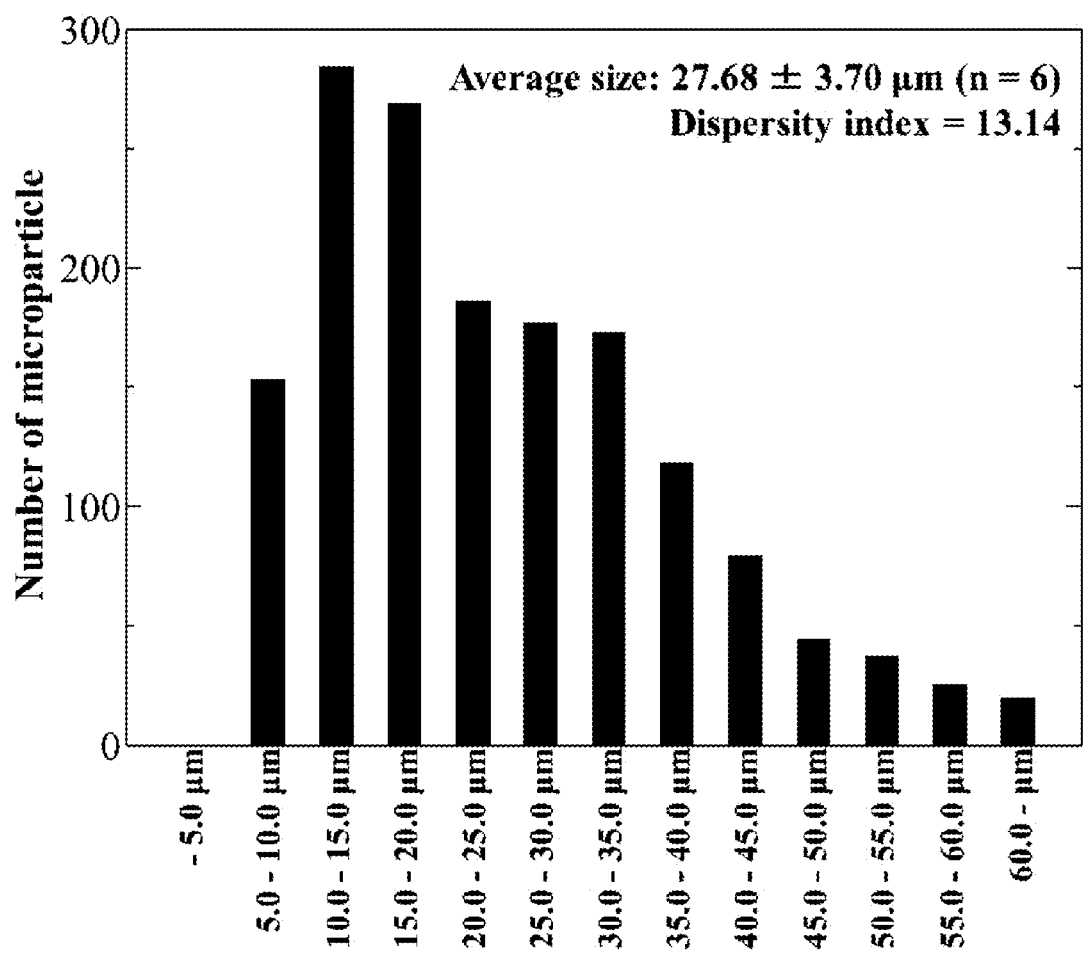
FIG. 2 is a graph showing the particle size distribution of microparticles.

FIG. 2 is a graph showing the particle size distribution of the microparticles.

Experiment 2

Visualization of GDNF Contained in Microparticles

In order to determine whether or not GDNF-CBP was contained in the microparticles, microparticles were prepared in the same manner as described above using GDNF-CBP labeled with a red fluorescent dye (Alexa 594).

Alexa 594-labeled GDNF-CBP was prepared using a normal protein fluorescent labeling method, and incorporated in the microparticles.

(B) in FIG. 1 is a fluorescence micrograph of the microparticles containing Alexa 594-labeled GDNF-CBP.

Since red fluorescence emitted from the microparticles was observed in the fluorescence micrograph (Note: (B) in FIG. 1 is in grayscale), it was confirmed that GDNF-CB was contained in the microparticles.

Experiment 3

Selective Controlled Release of GDNF Contained in Microparticles

In order to determine whether or not the release timing of GDNF-CBP contained in the microparticles can be controlled, release of GDNF-CBP from the microparticles immersed in a phosphate buffer (PBS) and collagenase-containing PBS was evaluated.

Figure 3:
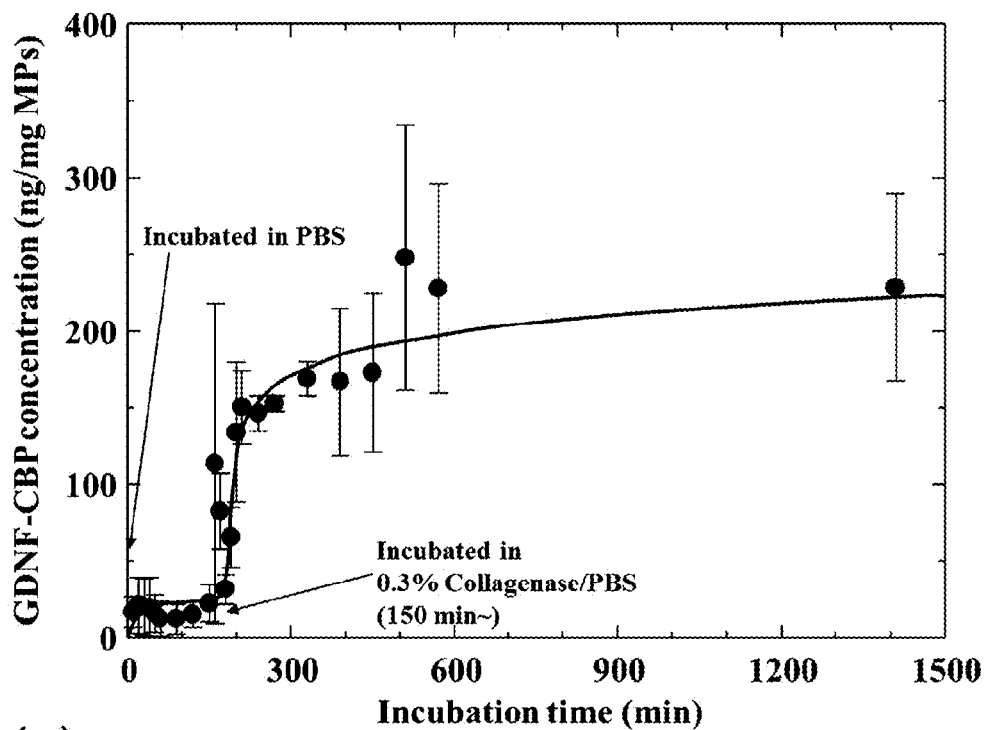
FIG. 3 shows graphs showing release of GDNF-CBP from microparticles immersed in PBS and microparticles immersed in collagenase-containing PBS including, wherein (A) shows the case where the collagenase concentration was 0.3%, and (B) shows the case where the collagenase concentration was 0.15%.
Figure 3:
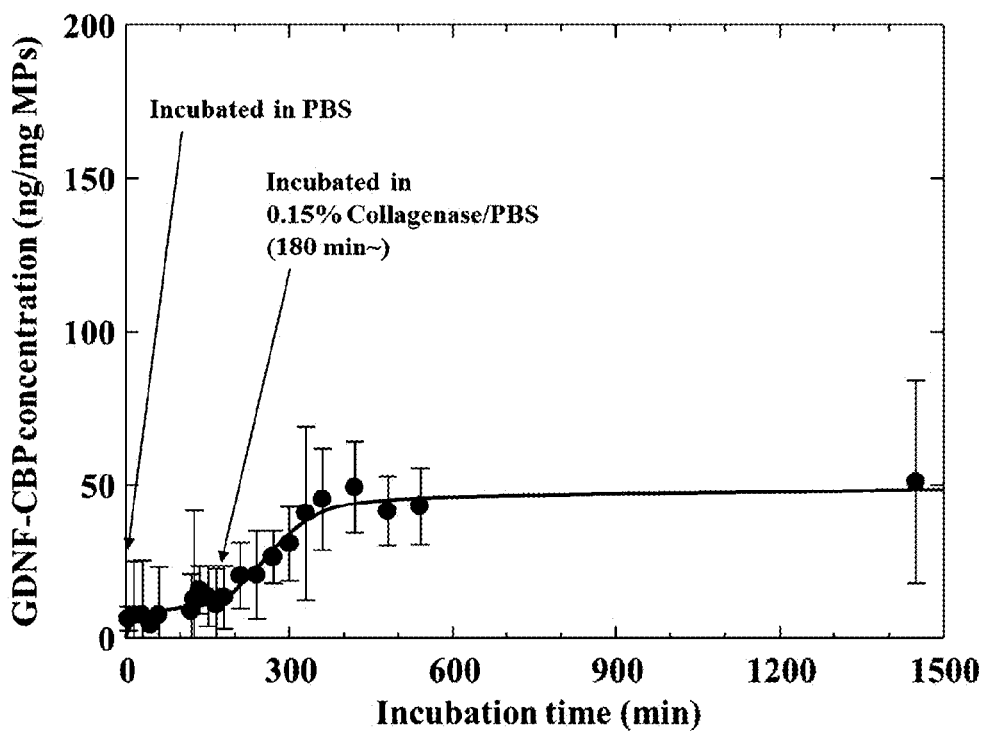
Figure 4:
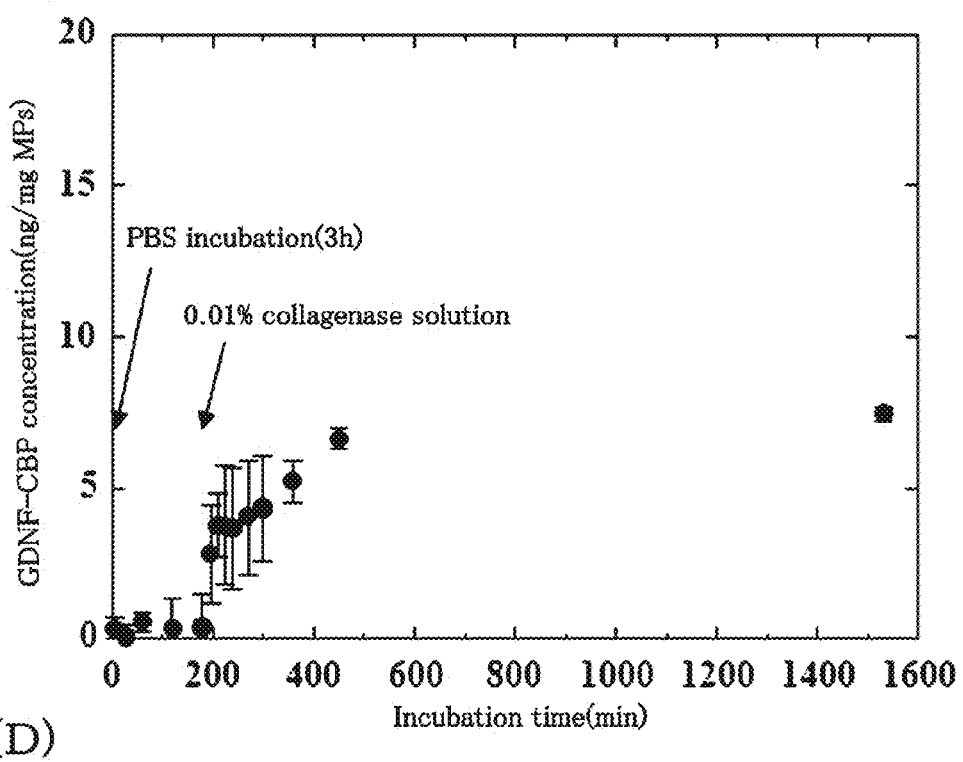
FIG. 4 shows a graph showing release of GDNF-CBP from microparticles immersed in PBS in which the collagenase concentration was 0.01% (see (C)), and a graph showing the presence or absence of release of GDNF-CBP when microparticles were immersed in PBS for 20 days (see (D)).
Figure 4:
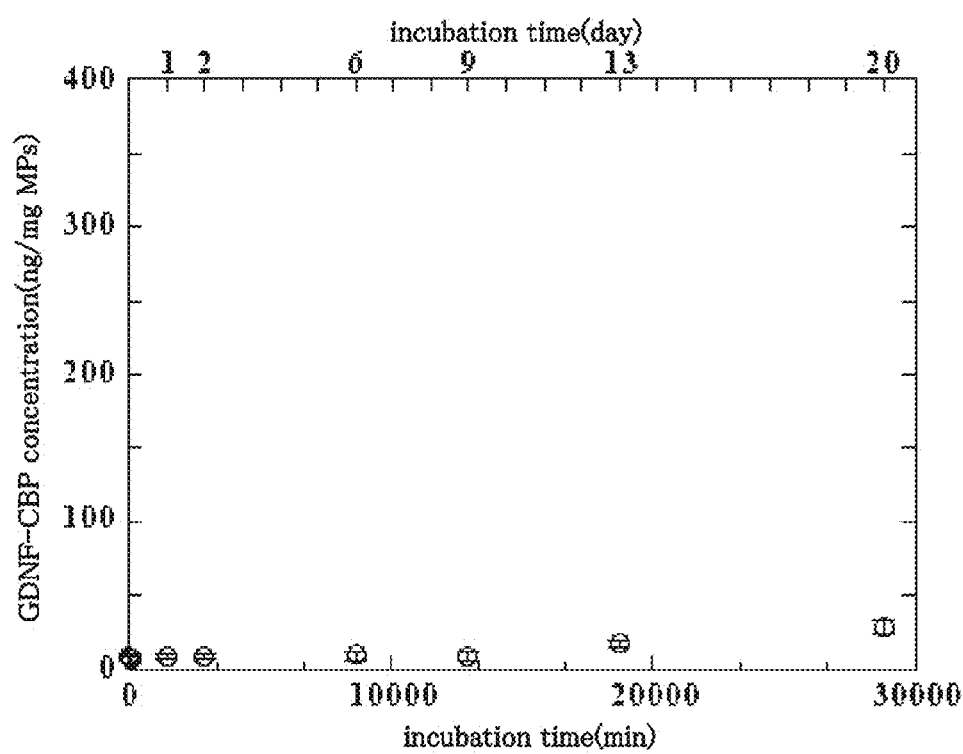

The results are shown in FIGS. 3 and 4.

The graph (A) in FIG. 3 shows the case where the collagenase concentration was 0.3%, and the graph (B) in FIG. 3 shows the case where the collagenase concentration was 0.15%.

The graph (C) in FIG. 4 shows the case where the collagenase concentration in PBS was 0.01%, and the graph (D) in FIG. 4 shows the case where the microparticles were immersed in PBS that did not include the collagenase for 20 days.

Since release of GDNF was not substantially observed in the graph (D) over 20 days, it was confirmed that controlled release of GDNF from the composition (microparticles) prepared in Experiment 1 occurred only in the presence of the collagenase.

As is clear from the graphs (A), (B), and (C) that differ in collagenase concentration, release of GDNF-CBP was not observed when the microparticles was immersed in PBS, and controlled release of GDNF-CBP was observed when the collagenase was added. The release rate of GDNF-CBP increased along with an increase in collagenase concentration.

The controlled release amount and the release rate when the collagenase concentration was 0.01% were smaller than those when the collagenase concentration was 0.15% or 0.3%. However, a sufficient controlled release effect was observed.

The amount of GDNF-CBP contained in 1 mg of the microparticles was 1.46±0.21 μg.

These results demonstrate that release of proteins can be controlled corresponding to degradation of collagen.

The release rate can be controlled by changing the collagenase concentration, or changing the thickness of PLGA (i.e., changing the thickness of the outer layer by changing the concentration of PLGA when preparing the microparticles).

Experiment 4

Cellular Regulation Due to GDNF Released From Microparticles

The activity of GDNF-CBP contained in the microparticles was determined.

A surfactant was used when preparing the microparticles.

A polyethylene glycol-polypropylene glycol-polyethylene glycol ternary block copolymer (manufactured by SIGMA ALDRICH, Pluronic-F68 or Pluronic-F127) was used as the surfactant.

The activity of proteins mixed with Pluronic-F68 or Pluronic-F127 was determined by a cell culture assay, and it was found that Pluronic-F68 and Pluronic-F127 do not affect the activity of proteins.

The activity of GDNF-CBP released from the microparticles was determined by a cell culture assay.

Figure 5:
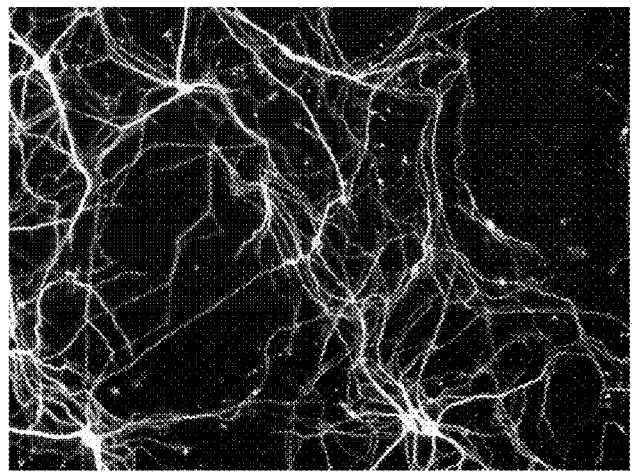
FIG. 5 shows micrographs when BDNF was added to neural stem/progenitor cells (cultured for 4 days), and GDNF-CBP released from microparticles was added (cultured for 7 days), wherein (1) shows a fluorescent image of the neural progenitor cells (β-tubulin III-positive cells), (2) shows a fluorescent image of mature nerve cells (MAP2-positive cells), and (3) shows a fluorescent image obtained by synthesizing the fluorescent images of the neural precursor cells, the mature nerve cells, and the nuclei.
Figure 5:
Figure 5:
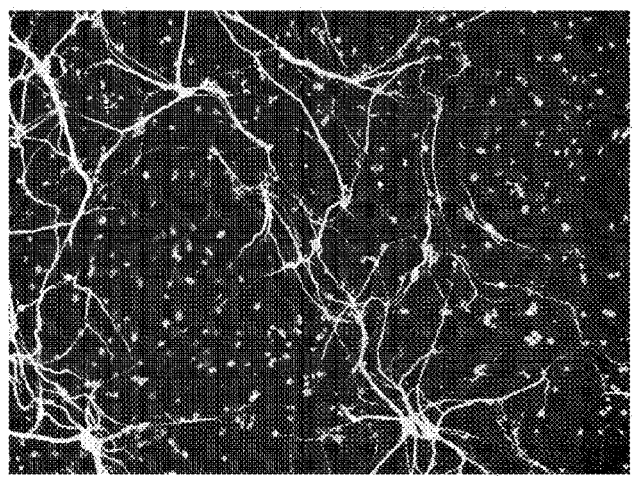

FIG. 5 shows fluorescent marker images when BDNF was added to neural stem/progenitor cells, and GDNF-CBP released from the microparticles prepared as described above was added on the seventh day, wherein (1) shows a fluorescent image of the neural progenitor cells, (2) shows a fluorescent image of the mature nerve cells, and (3) shows a fluorescent image obtained by synthesizing the fluorescent images of the neural progenitor cells, the mature nerve cells, and the nuclei.

It was thus confirmed that GDNF-CBP had an activity equal to that of commercially available GDNF.

These results suggest that the proteins are not inactivated during preparation of the microparticles, and GDNF is not inactivated in a state in which GDNF is contained in the microparticles.

The microparticles prepared in Experiment 1 were added to cells, and the cell differentiation state was determined.

The microparticles prepared in Experiment 1 were added to early nerve cells cultured for 4 days using a normal early nerve cell differentiation induction method (see FIG. 6, a: 50 μg, b: 100 μg, c: 150 μg), and the cells were cultured for 14 days in a medium to which 0.01% collagenase was added.

Note that the collagenase was added every day, and half of the medium was exchanged every 2 days.

Figure 6:
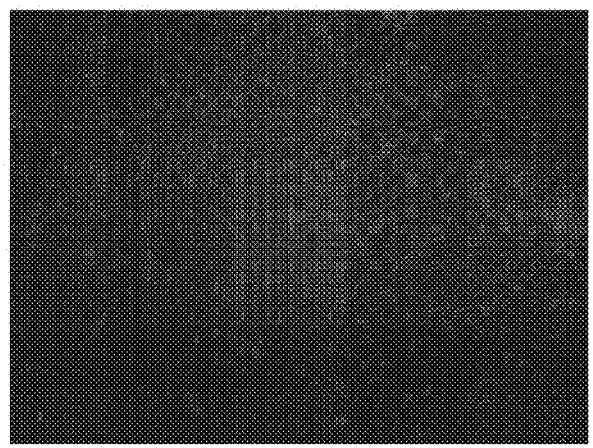
FIG. 6 shows fluorescent images of a mature nerve cell marker (MAP2) when the microparticles prepared in Experiment 1 were added to early nerve cells (a: 50 µg, b: 100 µg, c: 150 µg), and the cells were cultured for 14 days in a medium to which 0.01% collagenase was added.
Figure 6:
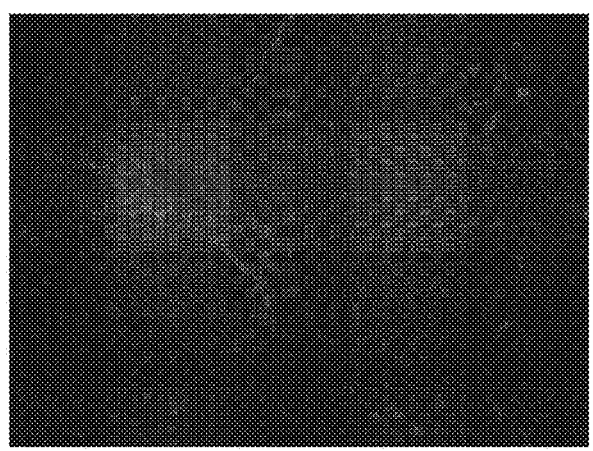
Figure 6:
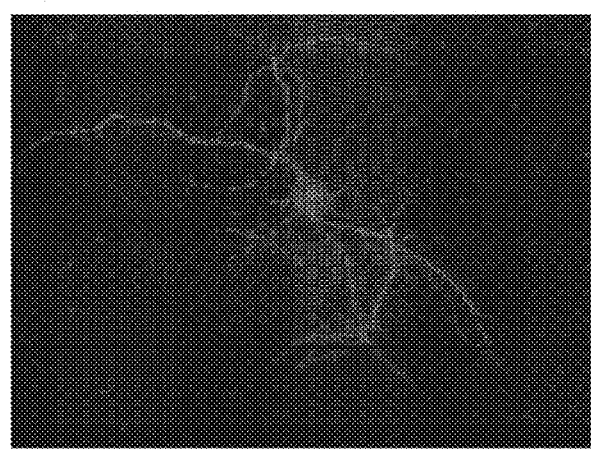

FIG. 6 shows a fluorescent image (grayscale) of only a nerve cell marker MAP2.

It was thus confirmed that the amount of GDNF released increased, and the ratio of mature nerve cells increased along with an increase in the amount of the microparticles added.

It was also confirmed from a fluorescent image of β-tubulin III (nerve cell marker) that neurite growth occurred along with an increase in the amount of the microparticles added.

When the microparticles were added, but the collagenase was not added, the presence of MAP2-positive cells was not observed, and the neurites of β-tubulin III-positive cells were thin and short (i.e., nerve growth was observed to only a small extent).

Figure 7:
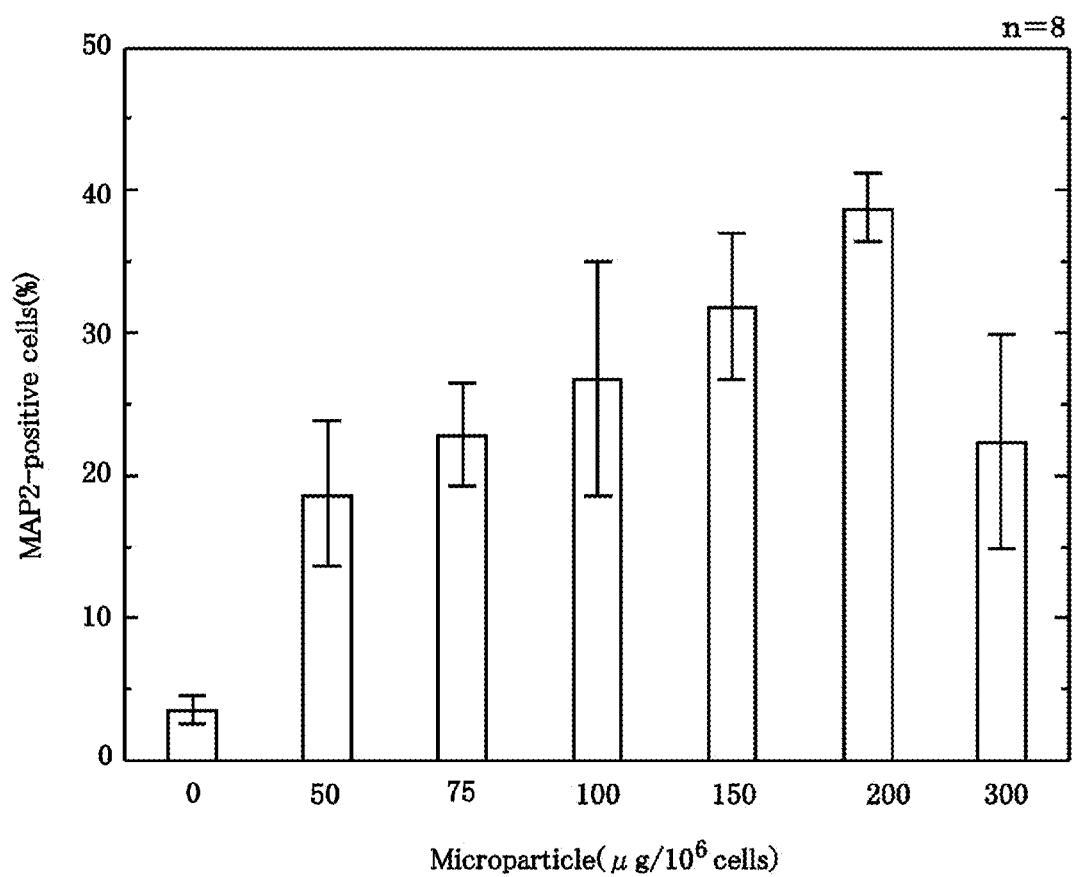
FIG. 7 shows a change in the ratio of MAP2-positive cells with respect to the amount of the microparticles prepared in Experiment 1.

FIG. 7 is a graph showing cellular differentiation induction by the microparticles prepared in Experiment 1 using the ratio of MAP2-positive cells.

The collagenase concentration was 0.01%.

The ratio of MAP2-positive cells increased along with an increase in the amount of the microparticles when the amount of the microparticles was added up to 200 $\mu g/10^6$ cells, but decreased to some extent when the amount of the microparticles was 300 $\mu g/10^6$ cells.

Since the microparticles were prepared in Experiment 1 using the surfactant, the effects on cells were determined.

Figure 8:
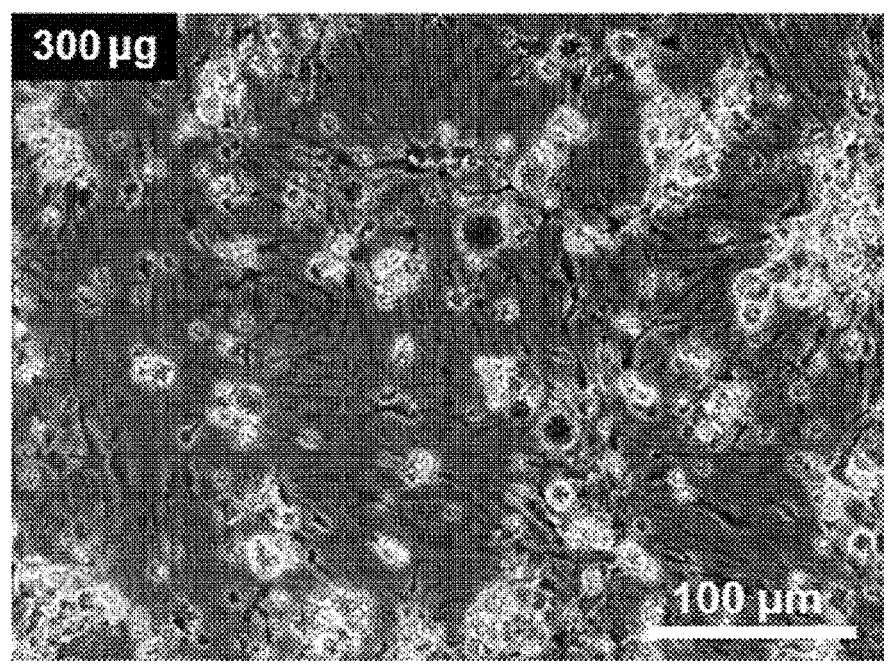
FIG. 8 shows the effects of the amount of the microparticles prepared in Experiment 1 on cells, wherein (a) shows a micrograph (after the cells were cultured for 7 days) when the amount of the microparticles was 300 μg, and (b) shows the viable cell count (control: microparticles were not added).
Figure 8:
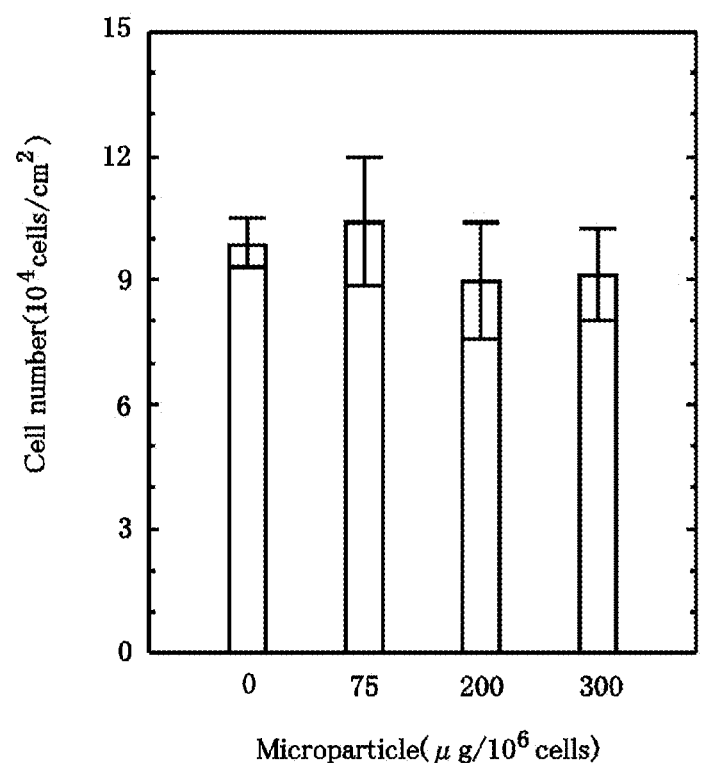

FIG. 8 shows comparison of count of the viable cell results when the microparticles prepared in Experiment 1 were added to neural stem/progenitor cells that were cultured in advance at various concentrations.

It was thus confirmed that the cells were not adversely affected when the amount of the microparticles was 300 $\mu g/10^6$ cells or less.

The effects of a microparticle storage method on activity were determined.

Figure 9:
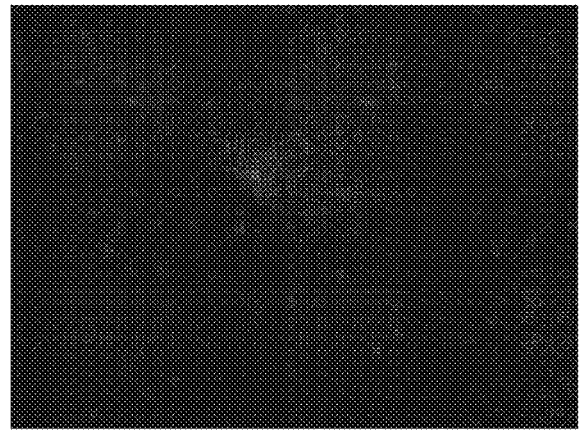
FIG. 9 shows fluorescent images of MAP2 after performing a differentiation induction assay for 2 weeks using the microparticles prepared in Experiment 1 that were stored under the condition (a), (b), or (c).
Figure 9:
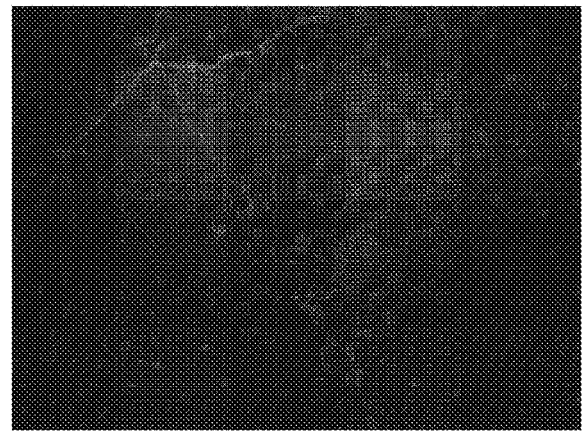
Figure 9:
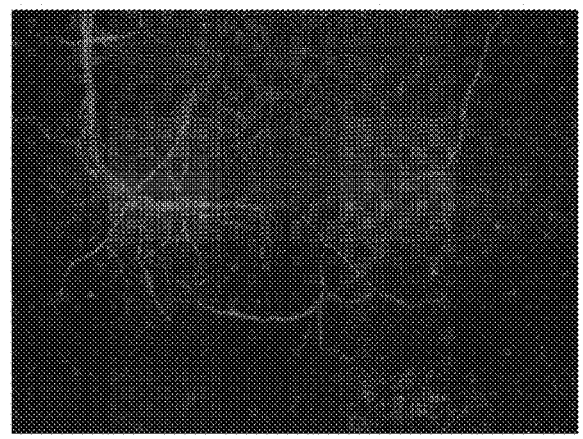

FIG. 9 shows fluorescent images of MAP2, wherein (a) shows an MAP2 fluorescent image after performing a differentiation induction assay for 2 weeks using the microparticles that were kept in PBS for 1 month in cold storage, (b) an MAP2 fluorescent image after performing a differentiation induction assay for 2 weeks using the microparticles that were stored in PBS for 1 month in a frozen state (−30° C.), and (c) an MAP2 fluorescent image after performing a differentiation induction assay for 2 weeks using the microparticles that were stored in PBS for 1 month in a lyophilized state.

Figure 10:
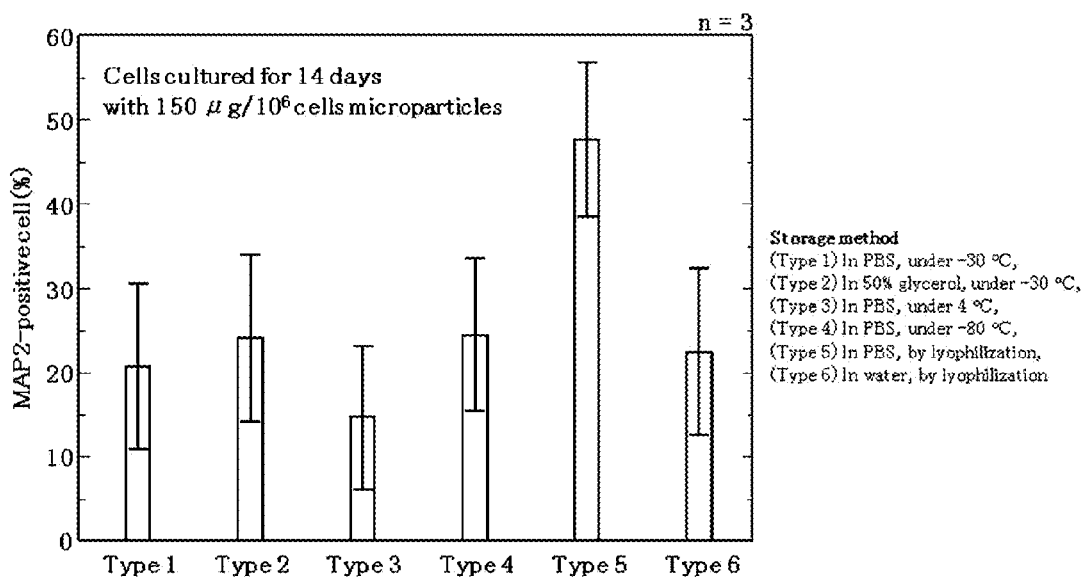
FIG. 10 shows the ratio (%) of MAP2-positive cells after storing the microparticles prepared in Experiment 1 under various storage conditions.

FIG. 10 shows the ratio of MAP2-positive cells determined by the differentiation induction assay (2 weeks) performed after storing the microparticles for 1 month under various storage conditions (Type 1 to Type 6).

It was thus confirmed that it is preferable to store the microparticles in a frozen state or a lyophilized state.

Microparticles were prepared in the same manner as in Experiment 1, except that hyaluronic acid (HAc) was used instead of collagen, and GDNF-HBP was caused to be supported on hyaluronic acid forming the inner layer.

Note that HBP refers to a peptide sequence that specifically binds to hyaluronic acid.

The outer layer was formed of PLGA in the same manner as in Experiment 1.

Figure 11:
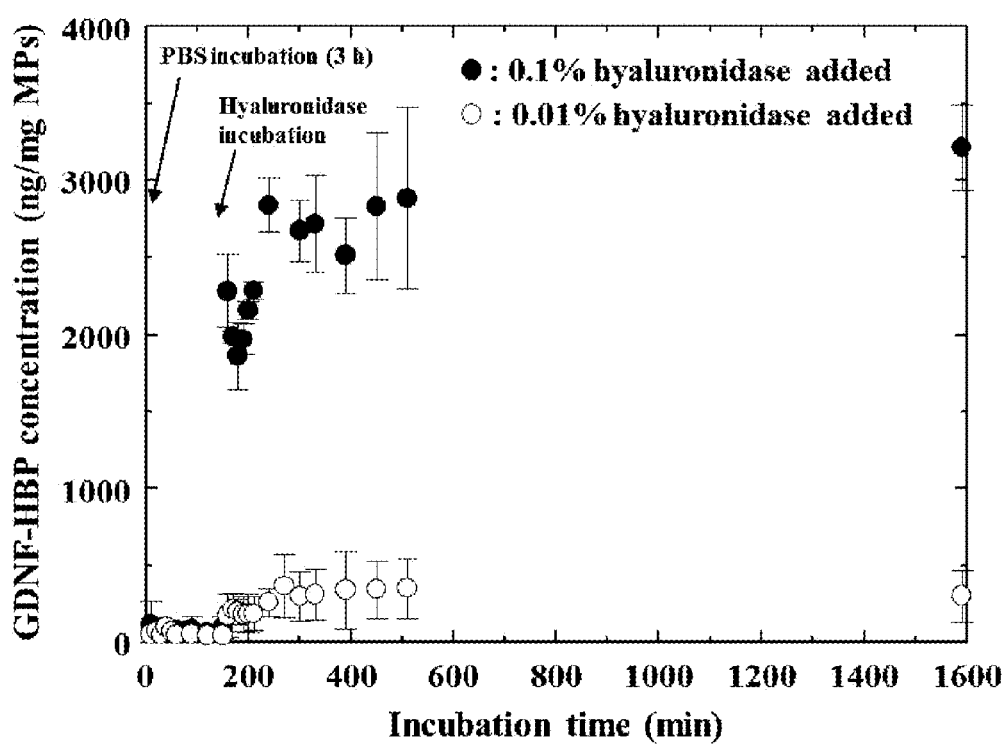
FIG. 11 is a graph showing release of GDNF-HBP (HBP: hyaluronic acid-binding peptide) when the microparticles prepared using hyaluronic acid (i.e., biodegradable substance that forms the inner layer and supports GDNF) were immersed in PBS to which hyaluronidase was added.

FIG. 11 is a graph showing a change in the concentration of GDNF-HBP released when the microparticles were immersed in PBS to which hyaluronidase was added at a concentration of 0.1% or 0.01%.

The results shown in FIG. 11 suggest that controlled release can be implemented when hyaluronic acid is used instead of collagen.

When neural stem/progenitor cells were cultured for 2 weeks in the presence of the microparticles, differentiation into mature nerve cells was observed. On the other hand, differentiation into mature nerve cells was not observed in a culture system to which a hyaluronidase was not added.

It was thus confirmed that the composition according to the embodiments of the invention can achieve its effects even when the biodegradable substance that forms the inner layer and supports proteins or the like is appropriately changed.

Figure 12:
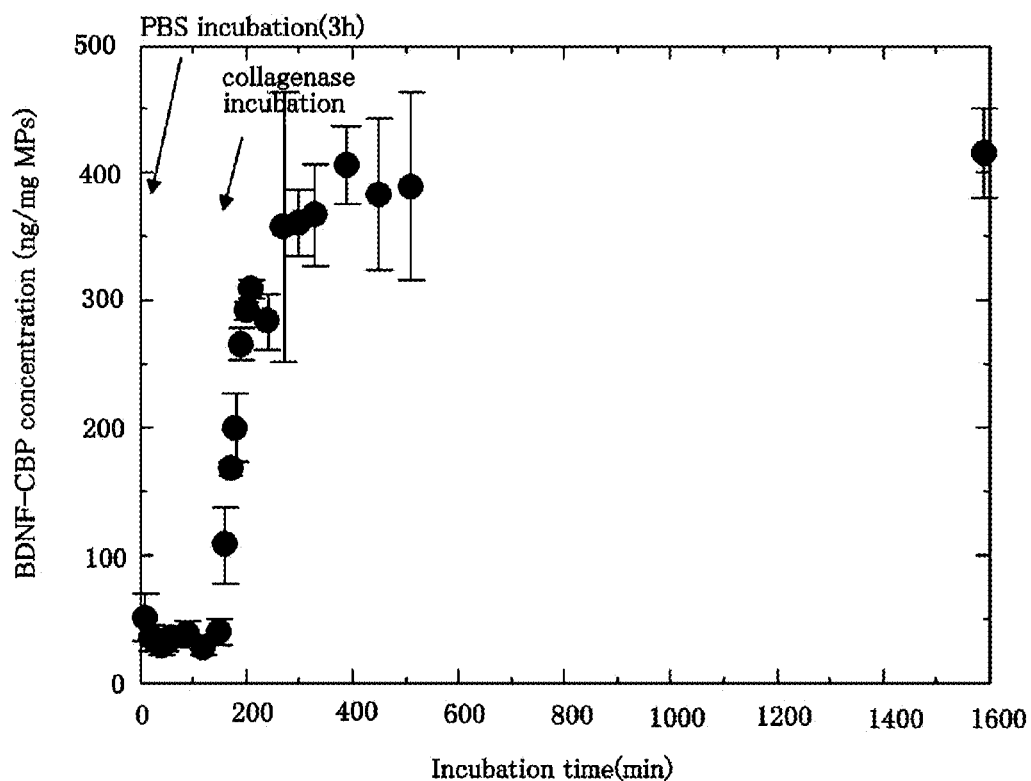
FIG. 12 is a graph showing release of GDNF-CBP from the microparticles prepared using brain-derived neurotrophic factor (BDNF) (i.e., physiologically active substance supported on collagen (inner layer)).

FIG. 12 shows the controlled release test results when using microparticles that were prepared in the same manner as in Experiment 1, except that brain-derived neurotrophic factor (BDNF) was used as the proteins supported on the inner layer.

It was thus confirmed that the physiologically active substance that is supported on the inner layer can be appropriately selected.

Figure 13:
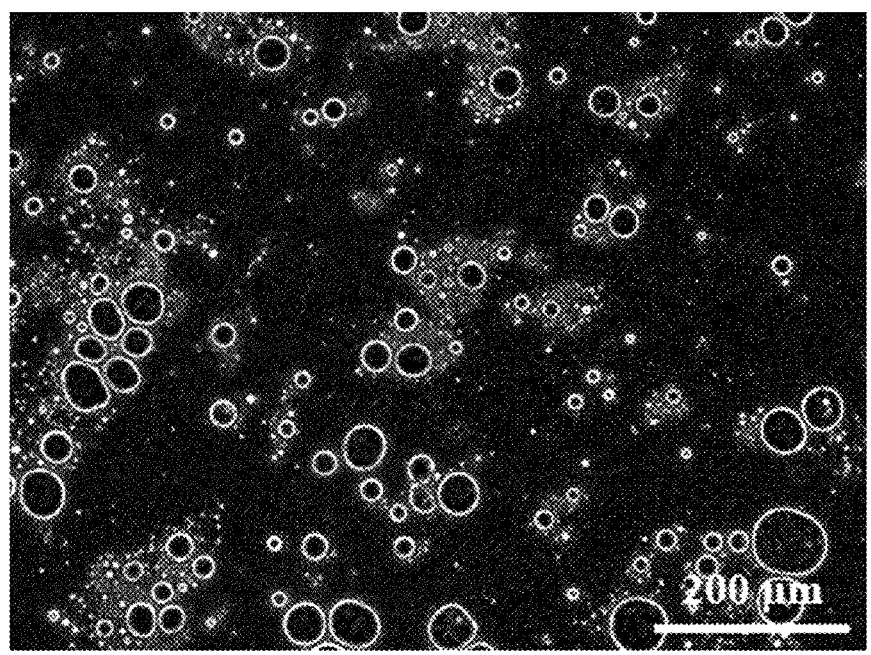
FIG. 13 is a micrograph of the microparticles prepared using PHA as the biodegradable polymer that forms the outer layer.

FIG. 13 shows microparticles prepared in the same manner as in Experiment 1, except that the outer layer was formed using a polyhydroxyalkanoic acid (PHA) instead of PLGA.

The outer layer could also be formed using poly-L-lactic acid (PLLA) instead of PLGA.

It was thus confirmed that the polymer that forms the outer layer can be appropriately selected.

An in vivo assay was performed using a rat.

A transplantation operation was performed on the striatum of the rat.

Neural stem/progenitor cells ($10^6$ cells), GDNF-containing PLGA/collagen microparticles, and Matrigel (commercially available product) were mixed, and injected into the striatum.

The transplantation tissue was collected (excised with a surgical knife) when a given period had elapsed. The RNA was extracted from the collected tissue, reverse-transcribed to cDNA, and subjected to PCR (RT-PCR).

The mRNA expression of the differentiation marker proteins was determined by this experiment.

Figure 14:
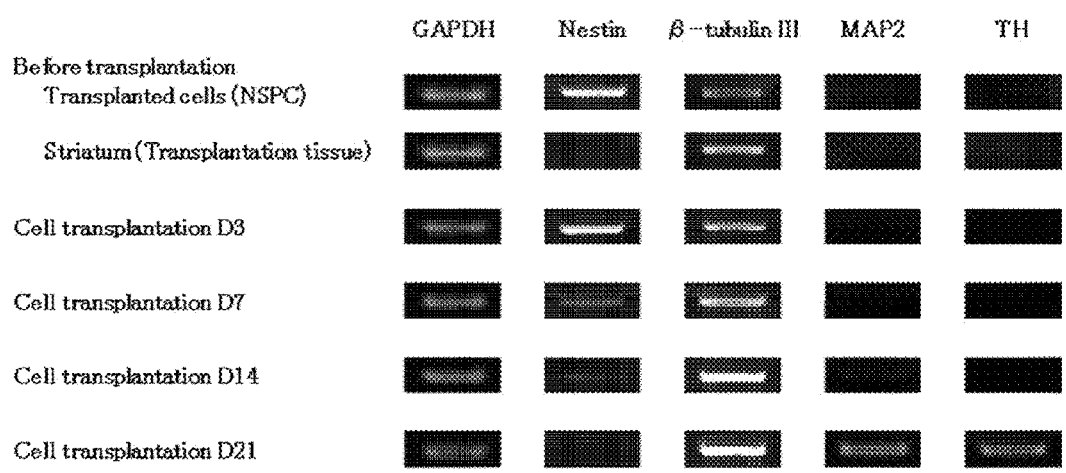
FIG. 14 shows the in vivo assay results obtained using a rat (i.e., the transplantation tissue was collected when a given period had elapsed after transplantation, and gene expression of the cells was analyzed).

The results are shown in FIG. 14.

GAPDH is a housekeeping gene, and the amount of gene between the samples when performing PCR was adjusted (normalization).

Nestin is a neural stem cell marker, and β-tubulin III is a nerve cell marker. These markers are expressed in each stage (from immature stage to mature stage).

MAP2 is a mature nerve cell marker.

TH (tyrosine hydroxylase) is a dopamine nerve cell marker.

The level of expression of Nestin in the tissue (striatum) was very small before transplantation, but increased after transplantation due to the transplanted cells.

The level of expression of Nestin then decreased. It is considered that this occurred due to differentiation of the transplanted cells.

The level of mRNA expression of Tubulin increased when 7 to 21 days had elapsed after transplantation.

It is considered that this is because the transplanted cells differentiated into nerve cells.

Since mRNA expression of MAP2 was observed on the fourteenth day after transplantation, and increased on the twenty-first day after transplantation, and mRNA expression of TH was observed on the twenty-first day after transplantation, it is considered that differentiation was induced when about one week had elapsed after transplantation due to the effects of the released GDNF.

INDUSTRIAL APPLICABILITY

Since the composition for controlled release of a physiologically active substance according to the embodiments of the invention can implement in situ control of release of the physiologically active substance in vivo, the composition is effective for efficiently inducing differentiation of transplanted stem cells, and regenerating the tissue. Therefore, the composition is useful for the treatment of intractable diseases, for example.

The invention claimed is:

1. A composition for controlled release of a physiologically active substance comprising:
    an inner layer that is formed of a biodegradable substance that supports a physiologically active substance, and
    an outer layer that is formed of a biodegradable substance that differs from that of the inner layer,
    the composition being in a shape of particles, the inner layer being an approximately spherical core, and the outer layer being a layer that covers the core,
    the physiologically active substance being a protein,
    the biodegradable substance that forms the inner layer being a natural biopolymer,
    the protein being supported on the natural biopolymer via a chimeric protein that is synthesized by fusing a substance into the protein, the substance undergoing strong intermolecular interaction with the natural biopolymer, an association constant between the protein and the natural biopolymer being $10^8$ to $10^{10}$ $M^{-1}$,
    the outer layer allowing the physiologically active substance supported on the inner layer to pass therethrough when the inner layer has undergone biodegradation.

2. The composition as defined in claim 1, the composition having an average particle size of 5 to 60 μm.

3. The composition as defined in claim 1, the biodegradable substance that forms the outer layer being an amorphous biodegradable polymer.

4. The composition as defined in claim 3, the natural biopolymer being collagen or hyaluronic acid, and the amorphous biodegradable polymer being poly(lactic-co-glycolic acid) (PLGA), polylactic acid (PLA), or a polyhydroxyalkanoic acid (PHA).

5. The composition as defined in claim 2, the biodegradable substance that forms the inner layer being a natural biopolymer, and the biodegradable substance that forms the outer layer being an amorphous biodegradable polymer.

* * * * *